United States Patent
Campbell et al.

[11] Patent Number: 5,868,704
[45] Date of Patent: Feb. 9, 1999

[54] BALLOON CATHETER DEVICE

[75] Inventors: Carey V. Campbell; Alvaro J. Laguna, both of Flagstaff; Mark S. Spencer, Phoenix, all of Ariz.

[73] Assignee: W. L. Gore & Associates, Inc., Newark, Del.

[21] Appl. No.: 673,635

[22] Filed: Jun. 26, 1996

Related U.S. Application Data

[63] Continuation-in-part of Ser. No. 532,905, Sep. 18, 1995, Pat. No. 5,752,934.

[51] Int. Cl.$^6$ .................................................. A61M 29/00
[52] U.S. Cl. .............................................. 604/96; 606/194
[58] Field of Search .............................. 604/96, 101, 264, 604/200; 606/194

[56] References Cited

U.S. PATENT DOCUMENTS

| | | |
|---|---|---|
| 4,106,509 | 8/1978 | McWhorter . |
| 4,403,612 | 9/1983 | Fogarty . |
| 4,573,966 | 3/1986 | Weikl et al. . |
| 4,637,396 | 1/1987 | Cook . |
| 4,650,466 | 3/1987 | Luther . |
| 4,702,252 | 10/1987 | Brooks et al. . |
| 4,706,670 | 11/1987 | Andersen et al. . |
| 4,713,070 | 12/1987 | Mano . |
| 4,737,219 | 4/1988 | Taller et al. . |
| 4,832,688 | 5/1989 | Sagae et al. . |
| 4,946,464 | 8/1990 | Pevsner . |
| 5,087,244 | 2/1992 | Wolinsky et al. . |
| 5,112,304 | 5/1992 | Barlow et al. . |
| 5,201,706 | 4/1993 | Noguchi et al. . |
| 5,213,576 | 5/1993 | Abiuso et al. . |
| 5,236,659 | 8/1993 | Pinchuk et al. . |
| 5,254,090 | 10/1993 | Lombardi et al. . |
| 5,256,143 | 10/1993 | Miller et al. . |
| 5,286,254 | 2/1994 | Shapland et al. . |
| 5,358,486 | 10/1994 | Saab . |
| 5,415,636 | 5/1995 | Forman . |
| 5,425,710 | 6/1995 | Khair et al. . |
| 5,429,605 | 7/1995 | Richling . |
| 5,456,661 | 10/1995 | Narciso . |
| 5,458,568 | 10/1995 | Racchini et al. . |
| 5,470,313 | 11/1995 | Crocker et al. . |
| 5,478,320 | 12/1995 | Trotta . |
| 5,499,980 | 3/1996 | Euteneuer . |
| 5,499,995 | 3/1996 | Teirstein . |
| 5,500,180 | 3/1996 | Anderson et al. . |
| 5,500,181 | 3/1996 | Wang et al. . |
| 5,512,051 | 4/1996 | Wang et al. . |

FOREIGN PATENT DOCUMENTS

| | | |
|---|---|---|
| 372088 | 6/1990 | European Pat. Off. . |
| 9614895 | 5/1996 | WIPO . |

*Primary Examiner*—Wynn Wood Coggins
*Assistant Examiner*—N. Kent Gring
*Attorney, Agent, or Firm*—Wayne D House

[57] ABSTRACT

Balloon catheters having the strength and maximum inflated diameter characteristics of an angioplasty balloon and having the recovery characteristics during deflation of an elastic embolectomy balloon. The balloon catheter can be made in very small sizes and has a lubricious and chemically inert outer surface. The balloon catheter is easy to navigate through tortuous passageways, is capable of rapid inflation and deflation and has high burst strengths. Balloon covers having these same characteristics are also described for use with conventional embolectomy balloons or angioplasty balloons.

18 Claims, 5 Drawing Sheets

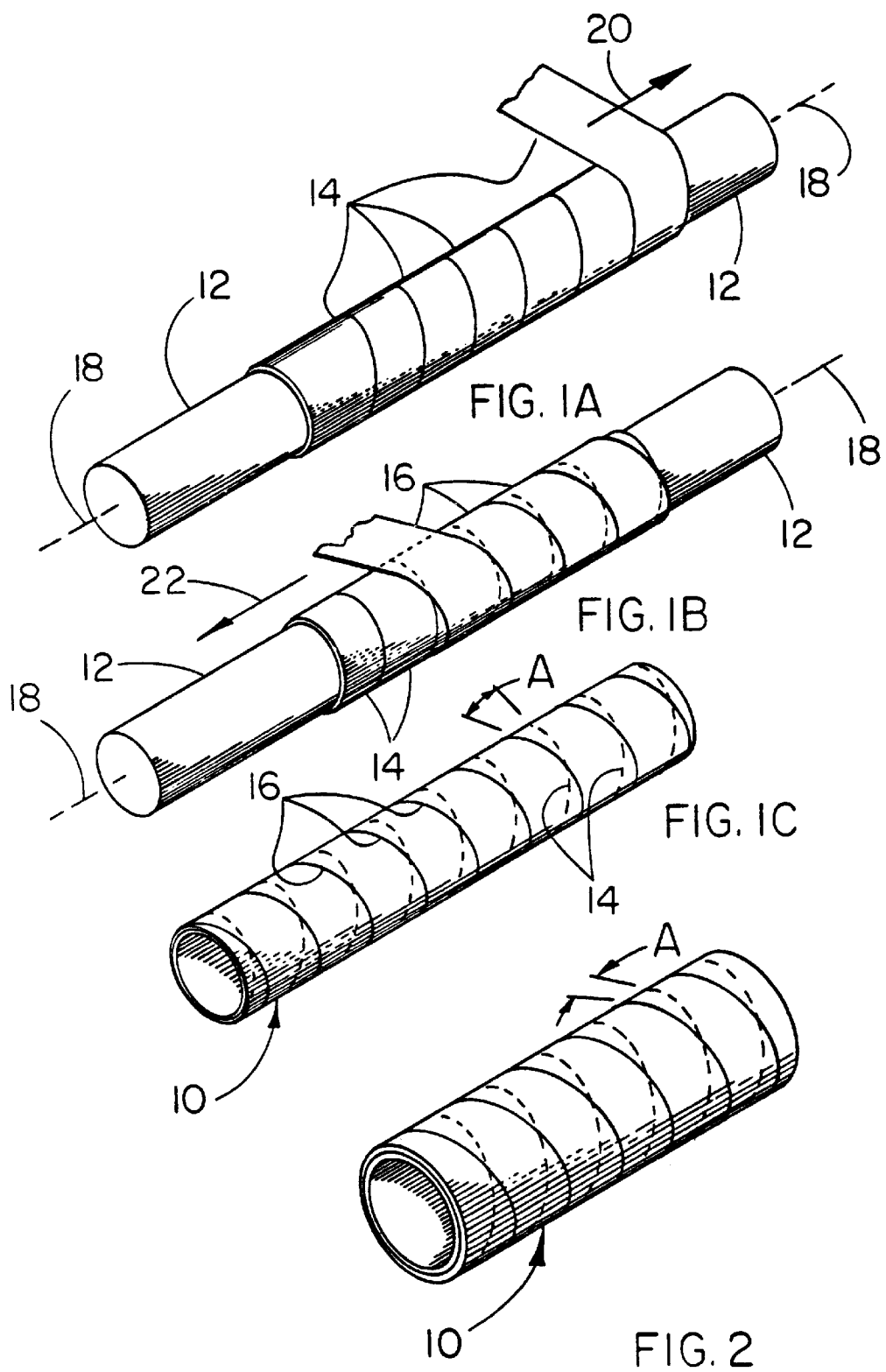

BALLOON CATHETER DEVICE

CROSS REFERENCE TO RELATED APPLICATIONS

This application is a continuation-in-part of application Ser. No. 08/532,905 filed Sep. 18, 1995, now U.S. Pat. No. 5,752,934.

FIELD OF THE INVENTION

The present invention relates to catheter balloons used in a variety of surgical procedures and to balloon covers for use with catheter balloons.

BACKGROUND OF THE INVENTION

Balloon catheters of various forms are commonly employed in a number of surgical procedures. These devices comprise a thin catheter tube that can be guided through a body conduit of a patient such as a blood vessel and a distensible balloon located at the distal end of the catheter tube. Actuation of the balloon is accomplished through use of a fluid filled syringe or similar device that can inflate the balloon by filling it with fluid (e.g., water or saline solution) to a desired degree of expansion and then deflate the balloon by withdrawing the fluid back into the syringe.

In use, a physician will guide the balloon catheter into a desired position and then expand the balloon to accomplish the desired result (e.g., clear a blockage, or install or actuate some other device). Once the procedure is accomplished, the balloon is then deflated and withdrawn from the blood vessel.

There are two main forms of balloon catheter devices. Angioplasty catheters employ a balloon made of relatively strong but generally inelastic material (e.g., polyester) folded into a compact, small diameter cross section. These relatively stiff catheters are used to compact hard deposits in vessels. Due to the need for strength and stiffness, these devices are rated to high pressures, usually up to about 8 to 12 atmospheres depending on rated diameter. They tend to be self-limiting as to diameter in that they will normally distend up to the rated diameter and not distend appreciably beyond this diameter until rupture due to over-pressurization. While the inelastic material of the balloon is generally effective in compacting deposits, it tends to collapse unevenly upon deflation, leaving a flattened, wrinkled bag, substantially larger in cross section than the balloon was when it was originally installed. Because of their tendency to assume a flattened cross section upon inflation and subsequent deflation, their deflated maximum width tends to approximate a dimension corresponding to one-half of the rated diameter times pi. This enlarged, wrinkled bag may be difficult to remove, especially from small vessels. Further, because these balloons are made from inelastic materials, their time to complete deflation is inherently slower than elastic balloons.

By contrast, embolectomy catheters employ a soft, very elastic material (e.g., natural rubber latex) as the balloon. These catheters are employed to remove soft deposits, such as thrombus, where a soft and tacky material such as latex provides an effective extraction means. Latex and other highly elastic materials generally will expand continuously upon increased internal pressure until the material bursts. As a result, these catheters are generally rated by volume (e.g., 0.3 cc) in order to properly distend to a desired size. Although relatively weak, these catheters do have the advantage that they tend to readily return to their initial size and dimensions following inflation and subsequent deflation.

Some catheter balloons constructed of both elastomeric and non-elastomeric materials have been described previously. U.S. Pat. No. 4,706,670 describes a balloon dilatation catheter constructed of a shaft made of an elastomeric tube and reinforced with longitudinally inelastic filaments. This device incorporates a movable portion of the shaft to enable the offset of the reduction in length of the balloon portion as the balloon is inflated. The construction facilitates the inflation and deflation of the balloon.

While balloon catheters are widely employed, currently available devices experience a number of shortcomings. First, as has been noted, the strongest materials for balloon construction tend to be relatively inelastic. The flattening of catheter balloons made from inelastic materials that occurs upon inflation and subsequent deflation makes extraction and navigation of a deflated catheter somewhat difficult. Contrastly, highly elastic materials tend to have excellent recovery upon deflation, but are not particularly strong when inflated nor are they self-limiting to a maximum rated diameter regardless of increasing pressure. This severely limits the amount of pressure that can be applied with these devices. It is also somewhat difficult to control the inflated diameter of these devices.

Second, in instances where the catheter is used to deliver some other device into the conduit, it is particularly important that a smooth separation of the device and the catheter balloon occur without interfering with the placement of the device. Neither of the two catheter devices described above is ideal in these instances. A balloon that does not completely compact to its original size is prone to snag the device causing placement problems or even damage to the conduit or balloon. Similarly, the use of a balloon that is constructed of tacky material will likewise cause snagging problems and possible displacement of the device. Latex balloons are generally not used for device placement in that they are considered to have inadequate strength for such use. Accordingly, it is a primary purpose of the present invention to create a catheter balloon that is small and slippery for initial installation, strong for deployment, and returns to its compact size and dimensions for ease in removal and further navigation following deflation. It is also believed desirable to provide a catheter balloon that will remain close to its original compact pre-inflation size even after repeated cycles of inflation and deflation. Other primary purposes of the present invention are to strengthen elastic balloons, to provide them with distension limits and provide them with a lubricious outer surface. The term "deflation" herein is used to describe a condition subsequent to inflation. "Pre-inflation" is used to describe the condition prior to initial inflation.

SUMMARY OF THE INVENTION

The present invention is an improved balloon catheter device for use in a variety of surgical procedures. The balloon catheter device of the present invention comprises a catheter tube having a continuous lumen connected to an inflatable and deflatable balloon at one end of the catheter tube. The catheter tube may have additional lumens provided for other purposes. The balloon can have a burst strength equal to or greater than that of conventional PTA catheter balloons. The balloon also has a maximum inflation diameter in a similar fashion to conventional PTA catheter balloons. The inventive balloon offers the recovery characteristics of a latex balloon that when deflated is of about the same maximum diameter as it was prior to inflation. This allows the inventive balloon to be withdrawn following deflation more easily than conventional PTA balloons which assume a flattened, irregular cross section following deflation and so have a deflated maximum diameter much larger than the pre-inflation maximum diameter. The balloon also has a smooth and lubricious surface which also aids in insertion and withdrawal. The inventive balloon possesses all of the above attributes even when made in small sizes heretofore commercially unavailable in balloon catheters without a movable portion of the catheter shaft or some other form of mechanical assist. The present invention eliminates the need for a movable portion of the shaft and associated apparatuses to aid in balloon deflation.

The present invention is made from polytetrafluoroethylene (hereinafter PTFE) materials and elastomeric materials. The PTFE is preferably porous PTFE made as taught by U.S. Pat. Nos. 3,953,566 and 4,187,390, both of which are incorporated by reference herein. An additional optional construction step, longitudinally compressing a porous PTFE tube prior to addition of the elastomeric component, allows the balloon or balloon cover to sufficiently change in length to enable the construction of higher pressure balloons, again without the need for mechanical assist. Particularly small sizes (useful in applications involving small tortuous paths such as is present in brain, kidney, and liver procedures) can be achieved by decreasing the wall thickness of the balloon via impregnation of a porous PTFE tube with silicone adhesive, silicone elastomer, silicone dispersion, polyurethane or another suitable elastomeric material instead of using a separate elastomeric member. Impregnation involves at least partially filling the pores of the porous PTFE. U.S. Pat. No. 5,519,172 teaches in detail the impregnation of porous PTFE with elastomers. In that this patent relates primarily to the construction of a jacket material for the protection of electrical conductors, the suitability of each of the various described materials for in vivo use as catheter balloon materials must be considered.

The balloon may be made from the materials described herein as a complete, stand-alone balloon or alternatively may be made as a cover for either conventional polyester PTA balloons or for latex embolectomy balloons. The use of the balloon cover of the present invention provides the covered balloon, regardless of type, with the best features of conventional PTA balloons and renders viable the use of elastic balloons for PTA procedures. That is to say, the covered balloon will have high burst strength, a predetermined maximum diameter, the ability to recover to substantially its pre-inflation size following deflation, and a lubricious exterior surface (unless it is desired to construct the balloon such that the elastomeric material is present on the outer surface of the balloon). The balloon cover substantially reduces the risk of rupture of an elastic balloon. Further, if rupture of the underlying balloon should occur, the presence of the balloon cover may serve to contain the fragments of the ruptured balloon. Still further, the inventive balloon and balloon cover can increase the rate of deflation of PTA balloons thereby reducing the time that the inflated balloon occludes the conduit in which it resides.

The present invention also enables the distension of a vessel and side branch or even a prosthesis within a vessel and its side branch without exerting significant force on the vessel or its branch. Further, it has been shown to be useful for flaring the ends of prostheses, thereby avoiding unwanted constrictions at the ends of the prostheses. Prostheses can slip along the length of prior art balloons during distension; the present invention not only reduces such slippage, it also can be used to create a larger diameter at the end of the graft than prior art materials.

The inventive balloon and balloon cover also maintain a substantially circular cross section during inflation and deflation in the absence of external constraint. Plus, the balloon and balloon cover can be designed to inflate at lower pressure in one portion of the length than another. This can be accomplished, for example, by altering the thickness of the elastomer content along the length of the balloon in order to increase the resistance to distension along the length of the balloon. Alternatively, the substrate tube may be constructed with varying wall thickness or varying amounts of helically-applied film may be applied along the tube length in order to achieve a similar effect.

Balloons of the present invention can also be constructed to elute fluids at pressures exceeding the balloon inflation pressure. Such balloons could have utility in delivering drugs inside a vessel.

A catheter balloon of the present invention is anticipated to be particularly useful for various surgical vascular procedures, including graft delivery, graft distension, stent delivery, stent distension, and angioplasty. It may have additional utility for various other surgical procedures such as, for example, supporting skeletal muscle left ventricular assist devices during the healing and muscle conditioning period and as an intra-aortic balloon.

BRIEF DESCRIPTION OF THE DRAWINGS

FIGS. 1A, 1B and 1C are perspective views describing manufacture of the tubular component forming the balloon or balloon cover of the present invention.

FIG. 2 is a perspective view describing the tubular component as it appears when inflated.

DETAILED DESCRIPTION OF THE INVENTION

Figure 3A:
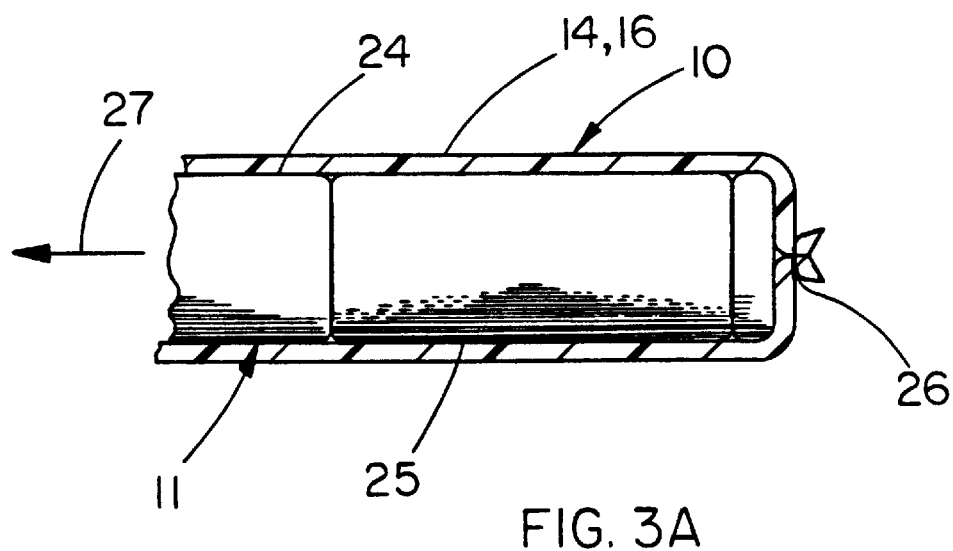
FIGS. 3A and 3B describe longitudinal cross sectional views of a balloon cover of the present invention without elastomer.

The catheter balloon and catheter balloon cover of the present invention are preferably made from porous PTFE films having a microstructure of interconnected fibrils.

These films are made as taught by U.S. Pat. Nos. 3,953,566 and 4,187,390. The balloon and balloon cover may also incorporate a porous PTFE substrate tube in the form, for example, of an extruded and expanded tube or a tube constructed of film containing at least one seam. Also, the balloon may be impregnated with an elastomeric material.

To form the balloon or balloon cover, both of which are made in the shape of a tube, a thin, porous PTFE film of the type described above is slit into relatively narrow lengths. The slit film is helically wrapped onto the surface of a mandrel in two opposing directions, thereby forming a tube of at least two layers. FIGS. 1A, 1B and 1C describe this procedure. FIG. 1A shows the first layer 14 of porous PTFE film helically wrapped over the mandrel 12 with the traverse direction of the wrap applied in a first direction 20 parallel to the longitudinal axis 18. The longitudinal axis of a balloon is defined as coincident with the longitudinal axis of the balloon catheter shaft, that is along the length of the shaft. Substantially parallel is defined as between about 0° and 45°, or between about 135° and 180°, with respect to the longitudinal axis of the catheter shaft and substantially circumferential is defined as between about 45° and 135° with respect to the longitudinal axis of the catheter shaft. FIG. 1B describes the application of the second layer of porous PTFE film 16 helically wrapped over the top of the first layer 14, wherein second layer 16 is wrapped in a second traverse direction 22 parallel to longitudinal axis 18 and opposite to the first traverse direction 20.

Preferably both layers 14 and 16 are wrapped with the same pitch angle measured with respect to the longitudinal axis but measured in opposite directions. If, for example, film layers 14 and 16 are applied at pitch angles of 70° measured from opposite directions with respect to longitudinal axis 18, then included angle A between both 70° pitch angles is 40°.

More than two layers of helically wrapped film may be applied. Alternate layers of film should be wrapped from opposing directions and an even number of film layers should be used whereby an equal number of layers are applied in each direction.

Following completion of film wrapping, the helically wrapped mandrel is placed into an oven for suitable time and temperature to cause adjacent layers to heat-bond together. After removal from the oven and subsequent cooling, the resulting film tube may be removed from the mandrel. The film tube is next placed over the balloon, tensioned longitudinally and affixed in place over the balloon.

During use, the inflated balloon or balloon cover 10 of the present invention has an increased diameter which results in included angle A being substantially reduced as shown by FIG. 2. The balloon or balloon cover thus reaches its pre-determined diametrical limit as included angle A approaches zero.

The inventive balloon or balloon cover 10 is reduced in diameter following deflation by one of two ways. First, tension may be applied to the balloon or balloon cover parallel to longitudinal axis 18 to cause it to reduce in diameter following deflation to the form described by FIG. 1C. The application of tension is necessary if low profile is desired. Alternatively, a layer of elastomer, applied to the luminal surface of the balloon 10 and allowed to cure prior to use of the balloon, will cause the balloon to retract to substantially its pre-inflation size shown by FIG. 1C following deflation. The elastomer may take the form of a coating of elastomer applied directly to the luminal surface of the balloon or balloon cover 10, or an elastomeric balloon such as a latex balloon or a silcone tube may be adhered to the luminal surface of the inventive balloon 10 by the use of an elastomeric adhesive. Alternatively, elastomer can be impregnated into the porous material to create a balloon or balloon cover.

Figure 3B:
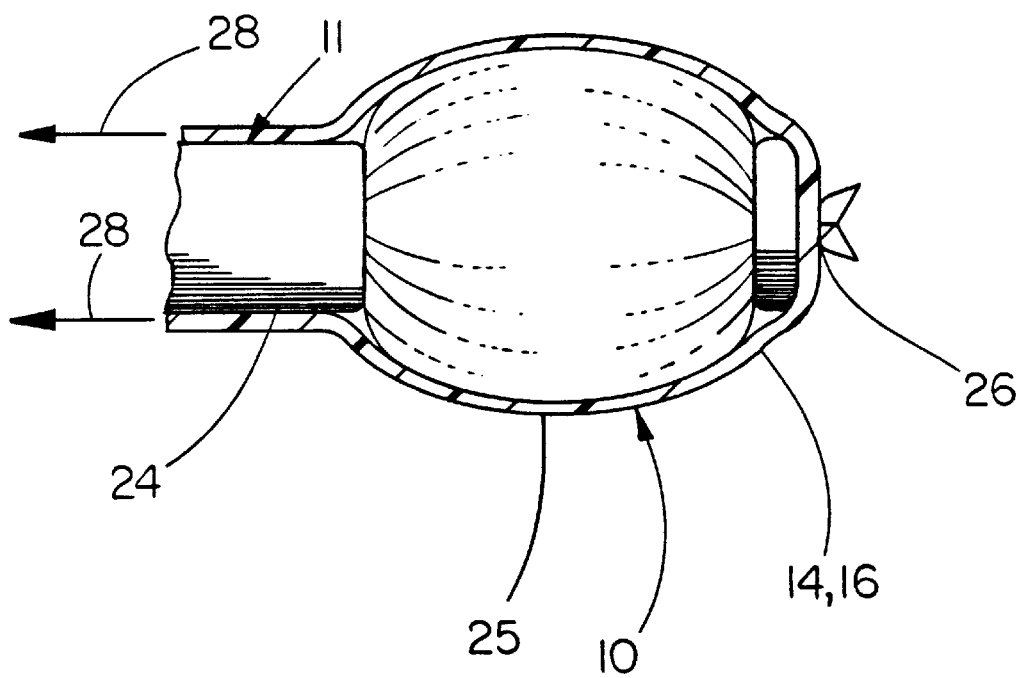
Figure 4A:
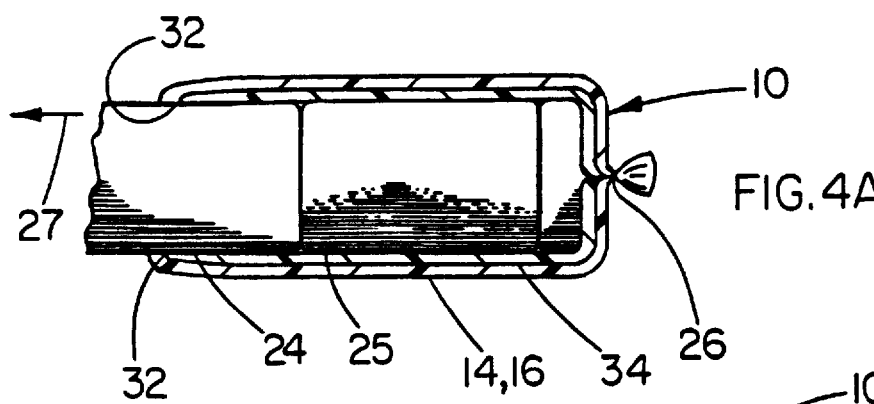
FIGS. 4A and 4B describe longitudinal cross sectional views of a balloon cover of the present invention incorporating a layer of elastomer.
Figure 4B:
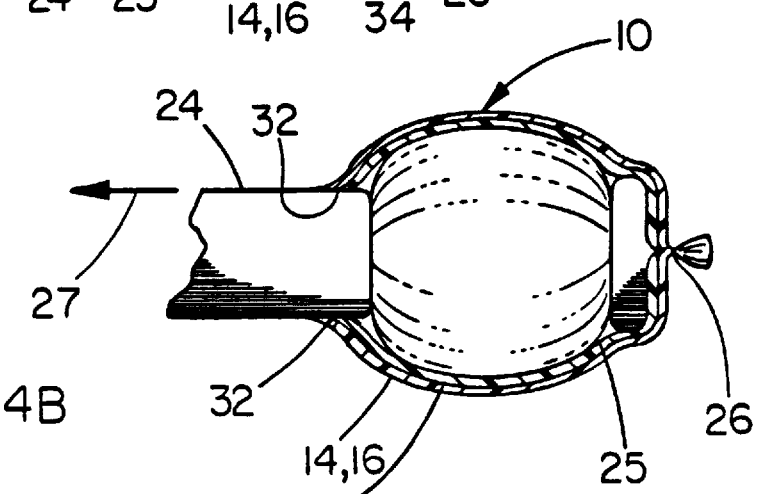

FIG. 3A describes a cross sectional view of a balloon cover 10 of the present invention in use with a conventional balloon catheter of either the angioplasty or embolectomy type. The figure describes a balloon cover without an elastomeric luminal coating. The balloon cover 10 is closed at distal end 26 of the balloon catheter 11. Balloon cover 10 extends in length part of the way to the proximal end 27 of balloon catheter 11 whereby balloon cover 10 completely covers catheter balloon 25 and at least a portion of the catheter 11. FIG. 3B describes the same balloon catheter 11 with catheter balloon 25 in an inflated state. Layers 14 and 16 of balloon cover 10 allow the cover to increase in diameter along with catheter balloon 25. During or following deflation of catheter balloon 25, tension is applied to the balloon cover 10 at the proximal end 27 of balloon catheter 11 as shown by arrows 28, thereby causing balloon cover 10 to reduce in diameter and substantially return to the state described by FIG. 3A. FIG. 4A describes a cross sectional view of a balloon cover 10 of the present invention wherein the balloon cover 10 has a liquid-tight layer of elastomer 34 applied to the inner surface of helically wrapped porous PTFE film layers 14 and 16. Balloon cover 10 is closed at distal end 26. The figure describes a ligated closure, such as by a thread or filament, however, other suitable closing means may be used. Proximal end 27 of balloon cover 10 is affixed to the distal end 32 of catheter 24. Balloon 25 may be of either the angioplasty or embolectomy type. If an elastomeric embolectomy balloon is used, it is preferred that the cover be adhered to the balloon by the use of an elastomeric adhesive to liquid-tight layer of elastomer 34. During inflation of balloon 25 as shown by FIG. 4B, helically wrapped porous PTFE film layers 14 and 16 and liquid-tight elastomer layer 34 increase in diameter along with balloon 25. During subsequent deflation, liquid-tight elastomer layer 34 causes helically wrapped porous PTFE film layers 14 and 16 to reduce in diameter as described previously, thereby returning substantially to the state described by FIG. 4A.

Figure 5A:
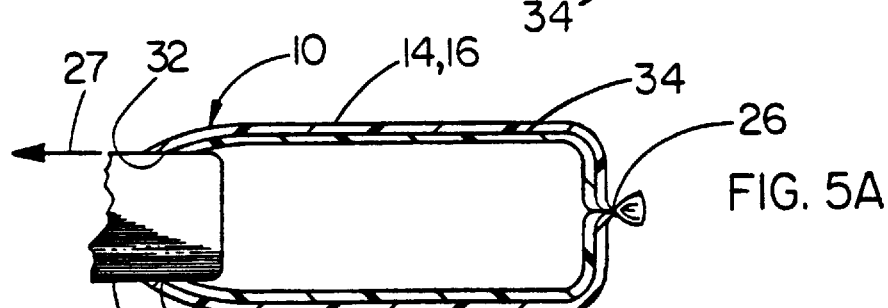
FIGS. 5A and 5B describe longitudinal cross sectional views of a catheter balloon of the present invention having the same material construction as the balloon cover of FIGS. 4A and 4B.
Figure 5B:
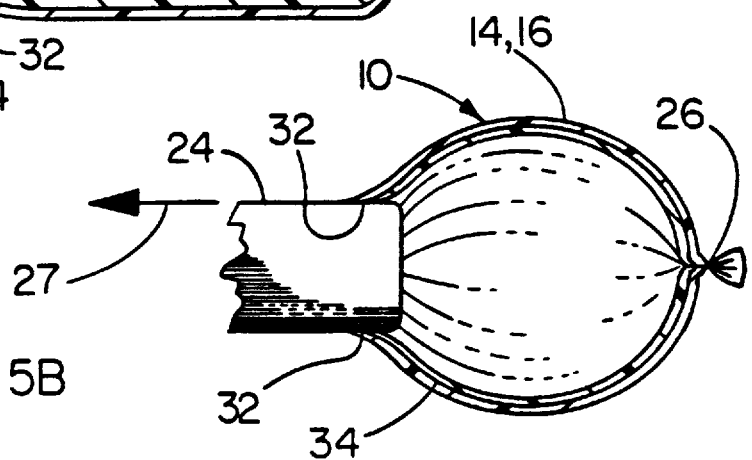

FIGS. 5A and 5B describe cross sectional views of a catheter balloon 10 made in the same fashion as the balloon cover described by FIGS. 4A and 4B. The presence of liquid-tight elastomer layer 34 allows this construction to function as an independent balloon 42 as described previously without requiring a conventional angioplasty or embolectomy balloon.

Figure 6A:
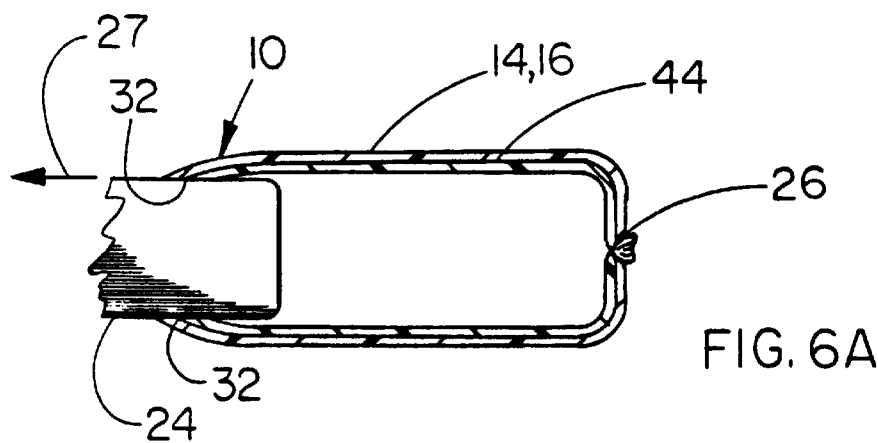
FIGS. 6A, 6B and 6C describe longitudinal cross sectional views of a catheter balloon of the type described by FIGS. 5A and 5B using a non-elastomeric material in place of the layer of elastomer.
Figure 6B:
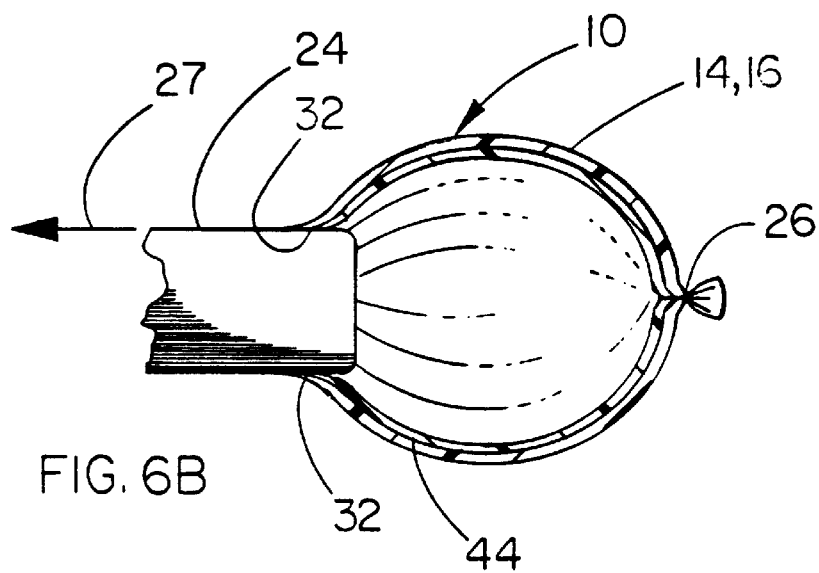
Figure 6C:
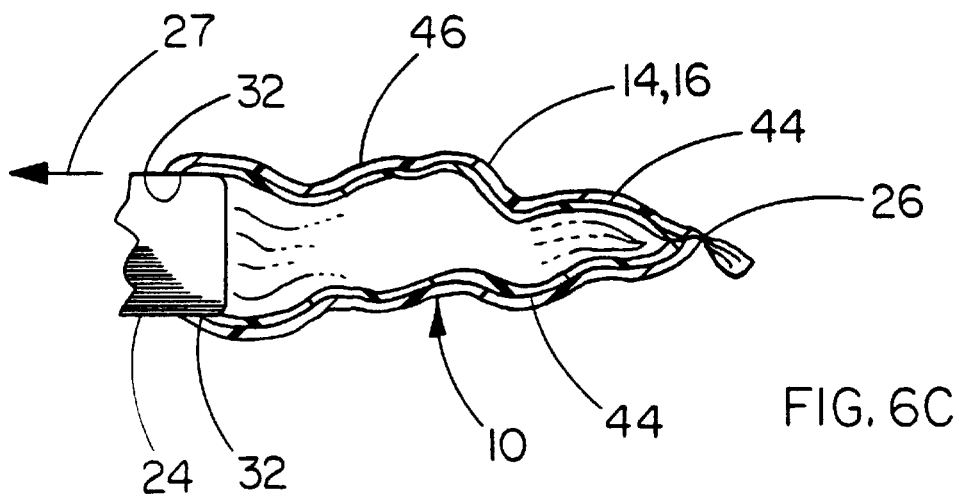

FIGS. 6A, 6B and 6C describe cross sectional views of an alternative embodiment of the catheter balloon 10 of the present invention. According to this embodiment helically wrapped porous PTFE film layers 14 and 16 are provided with a luminal coating 44 which is liquid-tight but is not elastomeric. The resulting balloon behaves in the fashion of a conventional angioplasty balloon but offers the advantages of a lubricious and chemically inert exterior surface. FIG. 6A describes the appearance of the balloon prior to inflation. FIG. 6B describes the balloon in an inflated state. As shown by FIG. 6C, following deflation, collapsed balloon 46 has a somewhat wrinkled appearance and an irregular transverse cross section in the same fashion as a conventional angioplasty balloon made from polyester or similar inelastic material.

It is also anticipated that the balloon and balloon cover of the present invention may be provided with an additional reinforcing mesh or braid on the exterior or interior surface of the balloon (or balloon cover), or more preferably between layers of the film whereby the mesh or braid is in the middle.

Alternatively, a mesh or braid of PTFE may be used as a balloon cover without including a continuous tube. A continuous tube does not include openings through its wall as does a conventional mesh or braid.

Figure 7:
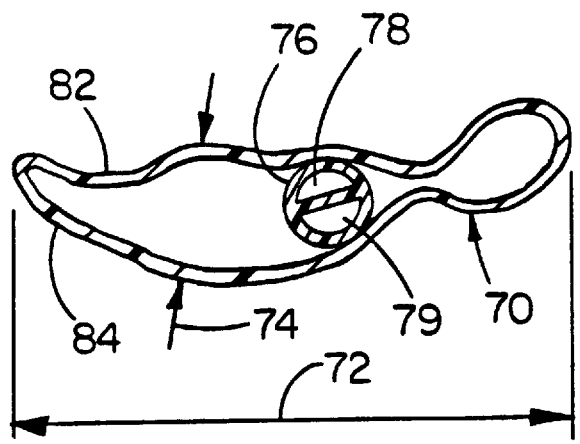
FIG. 7 describes a transverse cross section taken at the center of the length of a flattened, deflated angioplasty balloon which describes how the compaction efficiency ratio of the deflated balloon is determined.

The following examples describe in detail the construction of various embodiments of the balloon cover and catheter balloon of the present invention. Evaluation of these balloons is also described in comparison to conventional angioplasty and embolectomy balloons. FIG. 7 is provided as a description of the maximum dimension 72 and minimum dimension 74 (taken transversely to the longitudinal axis of the balloon) of a flattened, deflated angioplasty balloon 70 wherein the figure describes a transverse cross section of a typical flattened angioplasty balloon. The transverse cross section shown is meant to describe a typical deflated, flattened inelastic angioplasty balloon 70 having a somewhat irregular shape. Balloon 70 includes a catheter tube 76 having a guidewire lumen 78 and a balloon inflation lumen 79 and two opposing sides 82 and 84 of balloon 70. Maximum dimension 72 may be considered to be the maximum width of the flattened balloon 70 while minimum dimension 74 may be considered to be the maximum thickness across the two opposing sides 82 and 84 of the flattened balloon 70. All balloon and catheter measurements are expressed in terms of dimensions even if the shape is substantially circular.

Example 1

This example illustrates the use of a balloon cover of the present invention over a commercially available angioplasty balloon. The balloon cover provides a means of returning the angioplasty balloon close to its original compact geometry after inflation and subsequent deflation, as well as providing the known chemical inertness and low coefficient of friction afforded by PTFE.

The balloon used was a MATCH 35® Percutaneous Transluminal Angioplasty (PTA) Catheter model number B508-412, manufactured by SCHNEIDER (Minneapolis, Minn.). This balloon when measured immediately after being removed from the protective sheath provided by the manufacturer had a minimum dimension of 2.04 mm and a maximum dimension of 2.42 mm. These measurements were taken from approximately the center of the balloon, as defined by the midpoint between the circumferentially-oriented radiopaque marker bands located at both ends of the balloon. A Lasermike model 183, manufactured by Lasermike, (Dayton, Ohio) was used to make the measurements while the balloon was rotated about its longitudinal axis. The shaft onto which the balloon was attached had a minimum dimension of 1.74 mm and a maximum dimension of 1.77 mm measured adjacent to the point of balloon attachment closest to the center of the length of the shaft. The balloon, when inflated to 8 atmospheres internal water pressure, had a minimum dimension of 8.23 mm and a maximum dimension of 8.25 mm at the center of the length of the balloon. When deflated by removing the entire volume of water introduced during the 8 atmosphere pressurization, the balloon at its mid-length, had a minimum dimension of 1.75 mm, and a maximum dimension of 11.52 mm as measured using Mitutoyo digital caliper model CD-6"P. Upon completion of the measurements the balloon portion of the PTA catheter was carefully repackaged into the protective sheath.

The inventive balloon cover was made from a length of porous PTFE film made as described above cut to a width of 2.5 cm. The film thickness was approximately 0.02 mm, the density was 0.2 g/cc, and the fibril length was approximately 70 microns. Thickness was measured using a Mitutoyo snap gauge model 2804-10 and density was calculated based on sample dimensions and mass. Fibril length of the porous PTFE films used to construct the examples was estimated from scanning electron photomicrographs of an exterior surface of film samples.

This film was helically wrapped onto the bare surface of an 8 mm diameter stainless steel mandrel at an angle of approximately 70° with respect to the longitudinal axis of the mandrel so that about 5 overlapping layers of film cover the mandrel. Following this, another 5 layers of the same film were helically wrapped over the first 5 layers at the same pitch angle with respect to the longitudinal axis, but in the opposite direction. The second 5 layers were therefore also oriented at an approximate angle of 70°, but measured from the opposite end of the axis in comparison to the first 5 layers. Following this, another 5 layers of the same film were helically wrapped over the first and second 5 layers at the same bias angle with respect to the longitudinal axis as the first 5 layers, and then another 5 layers of the same film were helically wrapped over the first, second, and third 5 layers at the same bias angle with respect to the longitudinal axis as the second 5 layers. This resulted in a total of about 20 layers of helically wrapped film covering the mandrel.

The film-wrapped mandrel was then placed into an air convection oven set at 380° C. for 10 minutes to heat bond the layers of film, then removed and allowed to cool. The resulting 8 mm inside diameter film tube formed from the helically wrapped layers was then removed from the mandrel and one end was ligated onto a self-sealing injection site (Injection Site with Luer Lock manufactured by Baxter Healthcare Corporation, Deerfield, Ill.). A hole was created through the injection site, and the balloon end of the previously measured PTA catheter was passed through this hole, coaxially fitting the film tube over the balloon portion as well as a portion of the shaft of the PTA catheter. The film tube was approximately 25 cm in length. With the film tube over the PTA catheter and attached to the injection site, tension was applied manually to the free end of the film tube while the injection site was held fixed, causing the film tube to reduce in diameter and fit snugly onto the underlying segment of PTA catheter. Next, the film tube was ligated at the distal end of the PTA catheter shaft so that the balloon cover remained taut and snugly fit.

At this point the now covered balloon was measured in a deflated state. The minimum dimension was found to be 2.33 mm and the maximum dimension 2.63 mm. As before, these measurements were taken from approximately the center of the balloon, as defined by the midpoint between the radiopaque marker bands, and a Lasermike model 183, manufactured by Lasermike, (Dayton, Ohio) was used to make the measurements. The balloon, when inflated to 8 atmospheres internal water pressure had a minimum dimension of 7.93 mm and a maximum dimension of 8.06 mm at the center of the balloon. When deflated by removing the entire volume of water introduced during the 8 atmosphere pressurization, the balloon at its mid-length, had a minimum dimension of 1.92 mm and a maximum dimension of 11.17 mm. Next, tension was manually applied to the injection site causing the balloon cover to reduce the size of the underlying balloon, particularly along the plane of the 11.17 mm measurement taken previously. After the application of tension the covered balloon was measured again, and the minimum and maximum dimensions were found as 3.43 and 3.87 mm respectively.

This example shows that the balloon cover can be used effectively to compact a PTA balloon which was inflated and subsequently deflated to approximately the geometry of the balloon in an unused state. The measurements taken on the balloon (in both the uncovered and covered states) after inflation and subsequent deflation show that rather than undergoing a uniform circular compaction, the balloon tended to flatten. This flattening can be quantified by calculating the ratio of the minimum dimension to the maximum dimension measured after inflation and subsequent deflation. This ratio is defined as the compaction efficiency ratio. Note that a circular cross section yields a compaction efficiency ratio of unity. For this example, the uncovered balloon had a compaction efficiency ratio of 1.75 divided by 11.52, or 0.15. The balloon, after being provided with the inventive balloon cover, had a compaction efficiency ratio of 3.43 divided by 3.87, or 0.89. Additionally, the ratio of the maximum dimension prior to any inflation, to the maximum dimension after inflation and subsequent deflation, is defined as the compaction ratio. A balloon which has the same maximum dimension prior to any inflation, and after inflation and subsequent deflation, has a compaction ratio of unity. For this example, the uncovered balloon had a compaction ratio of 2.42 divided by 11.52, or 0.21. The balloon, after being provided with the inventive balloon cover, had a compaction ratio of 2.63 divided by 3.87, or 0.68.

Example 2

This example illustrates the use of a balloon cover over a commercially available latex embolectomy balloon. The balloon cover provides a defined limit to the growth of the embolectomy balloon, a substantial increase in burst strength, and the known chemical inertness and low coefficient of friction afforded by PTFE.

The balloon used was a Fogarty® Thru-Lumen Embolectomy Catheter model 12TL0805F manufactured by Baxter Healthcare Corporation (Irvine, Calf.). This natural rubber latex balloon when measured immediately after being removed from the protective sheath provided by the manufacturer had a minimum dimension of 1.98 mm and a maximum dimension of 2.02 mm. These measurements were taken from approximately the center of the balloon, as defined by the midpoint between the radiopaque marker bands. A Lasermike model 183, manufactured by Lasermike, (Dayton, Ohio) was used to make the measurements while the balloon was rotated about its longitudinal axis. The shaft onto which the balloon was attached had a minimum dimension of 1.64 mm and a maximum dimension of 1.68 mm measured adjacent to the point of balloon attachment closest to the center of the length of the shaft. The balloon, when filled with 0.8 cubic centimeters of water had a minimum dimension of 10.71 mm and a maximum dimension of 10.77 mm at the center of the balloon. When deflated by removing the entire volume of water introduced, the balloon at its midlength, had a minimum dimension of 1.97 mm and a maximum dimension of 2.04 mm. The balloon when tested using a hand-held inflation syringe had a burst strength of 60 psi.

Another embolectomy catheter of the same type was covered using a porous PTFE film tube made as described in Example 1. The method used to cover the embolectomy catheter was the same as that used to cover the PTA catheter in Example 1.

At this point, the now covered balloon was measured in a pre-inflated state. The minimum dimension was found to be 2.20 mm and the maximum dimension 2.27 mm. As before, these measurements were taken from approximately the center of the balloon, as defined by the midpoint between the radiopaque marker bands, and a Lasermike model 183, manufactured by Lasermike (Dayton, Ohio) was used to make the measurements. The balloon, when filled with 0.8 cubic centimeters of water had a minimum dimension of 8.29 mm and a maximum dimension of 8.34 mm at mid-length. When deflated by removing the entire volume of water introduced, the balloon at its mid-length, had a minimum dimension of 3.15 mm and a maximum dimension of 3.91 mm. Next, tension was manually applied to the injection site causing the balloon cover to reduce in size. After the application of tension the covered balloon was measured again, and the minimum and maximum dimensions were found as 2.95 and 3.07 mm respectively. The covered balloon was determined to have a burst strength of 188 psi, failing solely due the burst of the underlying embolectomy balloon. The inventive balloon cover exhibited no indication of rupture.

This example shows that the inventive balloon cover effectively provides a limit to the growth, and a substantial increase in the burst strength of an embolectomy balloon. The measurements taken on the uncovered balloon show that when filled with 0.8 cubic centimeters of water the balloon reached a maximum dimension of 10.77 mm. Under the same test conditions, the covered balloon reached a maximum dimension of 8.34 mm. The burst strength of the uncovered balloon was 60 psi while the burst strength of the covered balloon was 188 psi when inflated until rupture using a hand-operated liquid-filled syringe. This represents more than a three fold increase in burst strength.

Example 3

This example illustrates the use of a composite material in a balloon application. A balloon made from the composite material described below exhibits a predictable inflated diameter, high strength, exceptional compaction ratio and compaction efficiency ratio, as well as the known chemical inertness and low coefficient of friction afforded by PTFE.

A length of SILASTIC®R×50 Silicone Tubing manufactured by Dow Corning Corporation (Midland, Mich.) having an inner diameter of 1.5 mm and an outer diameter of 2.0 mm was fitted coaxially over a 1.1 mm stainless steel mandrel and secured at both ends. The silicone tubing was coated with a thin layer of Translucent RTV 108 Silicone Rubber Adhesive Sealant manufactured by General Electric Company (Waterford, N.Y.). An 8 mm inner diameter film tube made in the same manner described in Example 1 was fitted coaxially over the stainless steel mandrel and the silicone tubing. Tension was manually applied to the ends of the film tube causing it to reduce in diameter and fit snugly onto the underlying segment of silicone tubing secured to the stainless steel mandrel. With the film tube in substantial contact with the silicone tubing, this composite tube was gently massaged to ensure that no voids were present between the silicone tube and the porous PTFE film tube. Next the entire silicone-PTFE composite tube was allowed to cure in an air convection oven set at 35° C. for a minimum of 12 hours. Once cured, the composite tube was removed from the stainless steel mandrel. One end of the composite tube was then fitted coaxially over a section of 5 Fr catheter shaft taken from a model B507-412 MATCH 35® Percutaneous Transluminal Angioplasty (PTA) Catheter, manufactured by SCHNEIDER (Minneapolis, Minn.) and clamped to the catheter shaft using a model 03.3 RER Ear Clamp manufactured by Oetiker (Livingston, N.J.) such that a watertight seal was present. The distal end of the balloon was closed using hemostats for expediency, however, a conventional ligature such as waxed thread may be used to provide a suitable closure. In this manner a balloon catheter was fashioned, utilizing the silicone-PTFE composite tube as the balloon material.

At this point, the balloon was measured in a pre-inflated state. The minimum dimension was found to be 2.31 mm and the maximum dimension 2.42 mm. As before, these measurements were taken from approximately the midpoint of the balloon, and a Lasermike model 183, manufactured by Lasermike, (Dayton, Ohio) was used to make the measurements while the balloon was rotated about its longitudinal axis. The balloon, when inflated to 8 atmospheres internal water pressure, had a minimum dimension of 7.64 mm and a maximum dimension of 7.76 mm at the center of the balloon. When deflated by removing the entire volume of water introduced during the 8 atmosphere pressurization, the balloon at its mid-length, had a minimum dimension of 2.39 mm and a maximum dimension of 2.57 mm. The silicone-PTFE composite balloon when tested using a hand-held inflation device had a burst strength of 150 psi, reaching a maximum dimension of about 7.9 mm prior to rupture.

This example illustrates that the balloon made from the silicone-PTFE composite tube exhibited a predictable limit to its diametrical growth as demonstrated by the destructive burst strength test wherein the balloon did not exceed the 8 mm diameter of the porous PTFE film tube component. The compaction ratio as previously defined was 2.42 divided by 2.57, or 0.94, and the compaction efficiency ratio as previously defined was 2.39 divided by 2.57, or 0.93.

Example 4

This example describes the construction of a PTA balloon made by helically wrapping a porous PTFE film having a non-porous FEP coating over a thin porous PTFE tube.

The FEP-coated porous expanded PTFE film was made by a process which comprises the steps of:
a) contacting a porous PTFE film with another layer which is preferably a film of FEP or alternatively of another thermoplastic polymer;
b) heating the composition obtained in step a) to a temperature above the melting point of the thermoplastic polymer;
c) stretching the heated composition of step b) while maintaining the temperature above the melting point of the thermoplastic polymer; and
d) cooling the product of step c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

The FEP-coated porous PTFE film used to construct this example was a continuous (non-porous) film. The total thickness of the coated film was about 0.02 mm. The film was helically wrapped onto an 8 mm diameter stainless steel mandrel that had been coaxially covered with a porous expanded PTFE tube, made as taught by U.S. Pat. Nos. 3,953,566 and 4,187,390. The porous PTFE tube was a 3 mm inside diameter tube having a wall thickness of about 0.10 mm and a fibril length of about 30 microns. Fibril length is measured as taught by U.S. Pat. No. 4,972,846. The 3 mm tube had been stretched to fit snugly over the 8 mm mandrel. The FEP-coated porous PTFE film was then wrapped over the outer surface of this porous PTFE tube in the same manner as described by Example 1, with the FEP-coated side of the film placed against the porous PTFE tube surface. The wrapped mandrel was placed into an air convection set at 380° C. for 2.5 minutes, removed and allowed to cool, at which time the resulting tube was removed from the mandrel. One end of this tube was fitted coaxially over the end of a 5 Fr catheter shaft taken from a model number B507-412 PTA catheter manufactured by Schneider (Minneapolis, Minn.), and clamped to the catheter shaft using a model 03.3 RER Ear Clamp manufactured by Oetiker (Livingston, N.J.) such that a watertight seal was present. The resulting balloon was packed into the protective sheath which was provided by Schneider as part of the packaged balloon catheter assembly. The balloon was then removed from the protective sheath by sliding the sheath proximally off of the balloon and over the catheter shaft. Prior to inflation, the minimum and maximum diameters of the balloon were determined to be 2.25 and 2.61 mm. The distal end of the balloon was then closed using hemostats for expediency, however, a conventional ligature such as waxed thread could have been used to provide a suitable closure. When inflated to a pressure of 6 atmospheres, the minimum and maximum diameters were 8.43 and 8.49 mm. After being deflated the minimum and maximum diameters were 1.19 and 12.27 mm. These diameters resulted in a compaction ratio of 0.21 and a compaction efficiency of 0.10.

Example 5

This example describes a balloon constructed by impregnating silicone dispersion into a porous PTFE tube with helically applied porous PTFE film. A balloon made in this way exhibits a very small initial diameter, predictable inflated diameter, high strength, exceptional compaction ratio and compaction efficiency ratio, as well as the known chemical inertness and low coefficient of friction afforded by PTFE. The impregnation with silicone dispersion enables the construction of a thinner balloon. The use of a thin porous PTFE tube as a substrate provides longitudinal strength to resist elongation of the balloon at high pressures.

A longitudinally extruded and expanded porous PTFE substrate tube was obtained. The substrate tube was 1.5 mm inside diameter, having a wall thickness of about 0.17 mm and a fibril length of about 45 microns. The tube was fitted coaxially onto a 1.5 mm diameter stainless steel mandrel. Next, a length of porous expanded PTFE film was obtained that had been cut to a width of 2.54 cm. This film had a thickness of about 0.02 mm, a density of about 0.2 g/cc, and a fibril length of about 70 microns. Thickness was measured using a Mitutoyo snap gauge model No. 2804-10. The film bulk density was calculated based on dimensions and mass of a film sample. Density of non-porous PTFE was considered to be 2.2 g/cc. Fibril length of the porous PTFE film used to construct the example was estimated from scanning electron photomicrographs of an exterior surface of samples of the film.

This film was helically wrapped directly onto the bare metal surface of a 7 mm diameter stainless steel mandrel at about 65° with respect to the longitudinal axis of the mandrel so that about two overlapping layers of film covered the mandrel. Both edges of the film were colored with black ink in order to measure the pitch angles of the film during the construction or use of the completed balloon. Following this, another approximately two layers of the same film were helically wrapped over the first two layers. The second two layers were applied at the same bias angle with respect to the longitudinal axis, but in the opposite direction. This procedure was repeated three times, providing approximately 16 total layers of film. The film-wrapped mandrel was then placed into a convection oven set at 380° C. for 10 minutes to heat-bond the adjacent layers of film, then removed and allowed to cool. The resulting 7 mm inside diameter film tube formed from the helically wrapped layers of films was then removed from the mandrel.

This 7 mm inside diameter porous PTFE film tube was then fitted coaxially over the 1.5 mm inside diameter PTFE substrate tube and mandrel. The film tube was then tensioned longitudinally to cause it to reduce in diameter to the extent that it fit snugly over the outer surface of the 1.5 mm tube. The ends of this reinforced tube were then secured to the mandrel in order to prevent longitudinal shrinkage during heating. The combined tube and mandrel assembly was placed into an air convention oven set at 380° C. for 190 seconds to heat bond the film tube to the outer surface of the substrate tube. The reinforced tube and mandrel assembly was then removed from the oven and allowed to cool.

Additional porous PTFE film was then helically applied to outer surface of the reinforced tube to inhibit wrinkling of the tube in the subsequent step. The tube was then compressed in the longitudinal direction to reduce the tube length to approximately 0.6 of the length just prior to this compression step. Care was taken to ensure a high degree of uniformity of compression along the length of the tube. Wire was used to temporarily affix the ends of the tube to the mandrel. The mandrel-loaded reinforced tube with the additional helically applied film covering was then placed into a convention oven set at 380° C. for 28 seconds, removed from the oven and allowed cool.

The additional outer film was removed from the reinforced tube, followed by removing the reinforced tube from the mandrel. The reinforced tube was then gently elongated by hand to a length of about 0.8 of the length just prior to the compression step.

The reinforced tube was then ready for impregnation with silicone dispersion (Medical Implant Grade Dimethyl Silicone Elastomer Dispersion in Xylene, Applied Silicone Corp., PN 40000, Ventura, Calif.). The silicone dispersion was first prepared by mixing 2.3 parts n-Heptane (J. T. Barker, lot #J07280) with one part silicone dispersion. Another mixture with n-Heptane was prepared by mixing 0.5 parts with 1 part silicone dispersion. Each mixture was loaded into an injection syringe.

The dispensing needle of each of the injection syringes was inserted inside one end of the reinforced tube. Wire was used to secure the tube around the needles. One of the dispensing needles was capped and the syringe containing the 2.3:1 silicone dispersion solution was connected to the other. The solution was dispensed inside the reinforced tube with about 6 psi pressure. Pressure was maintained for approximately one minute, until the outer surface of the tube started to become wetted with the solution, indicating that the dispersion entered the pores of the PTFE material. It was ensured that the silicone dispersion coated the inside of the PTFE tube. At this point, the syringe was removed, the cap was removed from the other needle, and the syringe containing the 0.5:1 silicone dispersion solution was connected to the previously-capped needle. This higher viscosity dispersion was then introduced into the tube with the syringe, displacing the lower viscocity dispersion through the needle at the other end, until the higher viscosity dispersion began to exit the tube through the needle. After ensuring that the tube was completely filled with dispersion, both needles were capped. Curing of the silicone dispersion was effected by heating the assembly in a convection oven set at 150° C. for a minimum of one hour. The solvent evaporated during the curing process, thereby recreating the lumen in the tube. The impregnated reinforced tube was removed from the oven and allowed to cool. Both ends of the tube were opened and the 0.5:1 silicone dispersion solution was injected in one end to again fill the lumen, the needle ends were then capped, then the dispersion was cured in the same manner as described above. At this point the balloon construction was complete.

The above-described process preserved PTFE as the outermost surface of the balloon. Alternatively, longer impregnation times or higher injection pressures during the initial impregnation could cause more thorough wetting of the PTFE structure with the silicone dispersion, thereby driving more dispersion to the outermost surface of the balloon.

Figure 8:
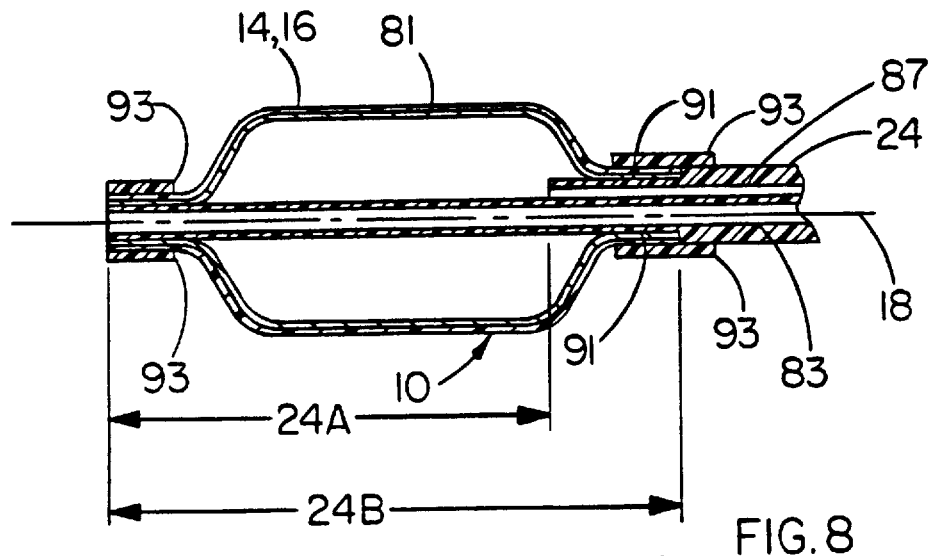
FIG. 8 describes a longitudinal cross section of a balloon affixed to the shaft of a dual lumen catheter, the balloon having a first PTFE material oriented substantially parallel to the longitudinal axis of the balloon and a second PTFE material oriented substantially circumferential to the longitudinal axis, wherein the PTFE materials is impregnated with an elastomer.
Figure 8A:
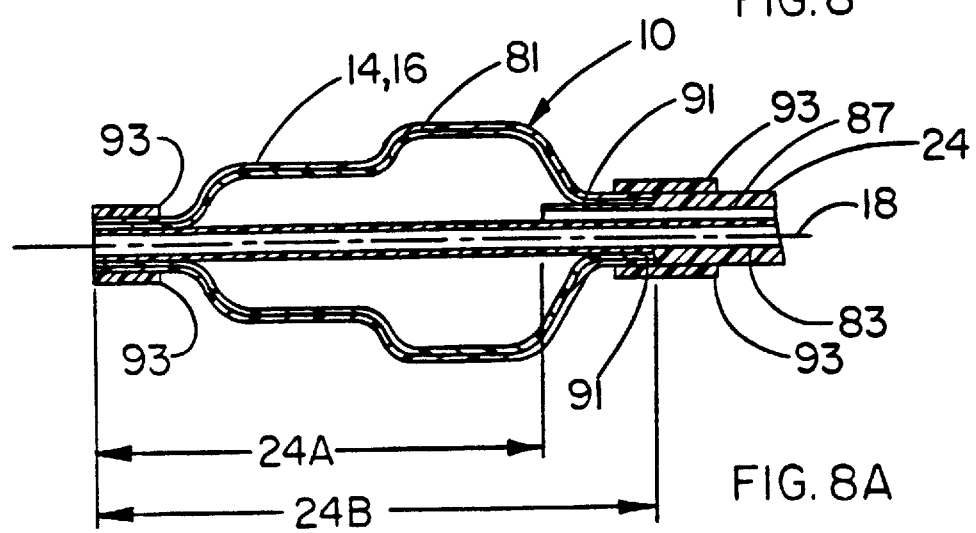
FIG. 8A describes a longitudinal cross section of an alternative embodiment to that of FIG. 8 wherein the balloon during inflation exhibits a larger diameter at a first portion of its length than at a second portion of its length.

The balloon was then ready for mounting on a 5 Fr catheter shaft obtained from a balloon dilatation catheter (Schneider Match 35 PTA Catheter, 6 mm dia., 4 cm length, model no. B506-412) This balloon was mounted on the 1.67 mm diameter catheter shaft as described by FIG. 8. Both ends of the balloon were mounted to the shaft. The catheter tip portion plus the balloon of the balloon dilatation catheter were cut off in the dual lumen portion of the shaft leaving only the catheter shaft 24. Guidewires serving as mandrels (not shown) were inserted into both lumens of the shaft. A 0.32 mm mandrel was inserted into the inflation lumen 87 and a 0.6 mm mandrel was inserted into the wire lumen 83. The portion 24A of the shaft 24 containing the inflation lumen 87 was shaved off longitudinally to a length approximately 1 cm longer than the length of the balloon to be placed on the shaft; therefore, this portion 24A of the shaft 24 then contained only the wire lumen 83 which possessed a semi-circular exterior transverse cross section. (The extra 1 cm length accommodates room for a tip portion of the catheter, without a balloon covering, in the final assembly.) With the mandrels still in place, portion 24B of the shaft 24 was inserted for about 30 seconds into a heated split die containing 1.5 mm diameter bore when the dies were placed together. The dies were heated to a temperature of 180° C. to form the semicircular cross sectional shape of the portion of the shaft into a round 1.5 mm cross section and to create a landing 91 in the area proximal to the distal end of the inflation lumen 87. Next, the balloon 10 (having circumferentially oriented film layers 14 and 16, and longitudinally oriented substrate tube 81) was slipped over the modified distal end of the shaft 24 such that the proximal end of the balloon 10 was approximately 0.5 cm from the end of the landing 91. This approximately 0.5 cm segment of the landing 91 adjacent to the abutment was primed for fifteen seconds (Loctite Prism™ Primer 770, Item #18397, Newington, Conn.) and then cyanoacrylate glue (Loctite 4014 Instant Adhesive, Part #18014, Rocky Hill, Conn.) was applied to that segment. The balloon 10 was moved proximally such that the proximal end of the balloon abutted against the end of the landing 91 and the glue was allowed to set. The distal end of the balloon 10 was attached in the same manner, while ensuring against wrinkling of the balloon during the attachment. At this point, a radiopaque marker could have been fitted at each end of the balloon. The last step in the mounting process involved securing the ends of the balloon with shrink tubing 93 (Advanced Polymers, Inc., Salem, N.H., polyester shrink tubing - clear, item #085100CST). Approximately 0.25 cm of the proximal end of the balloon and approximately 0.75 cm of the shaft adjacent to the end of the balloon were treated with the same primer and glue as described above. Approximately 1 cm length of shrink tubing 93 was placed over the treated regions of the shaft 24 and balloon 10. The same process was followed to both prepare the distal end the balloon and the adjacent modified shaft portion and to attach another approximately 1 cm length of shrink tubing 93. The entire assembly was then placed into a convection oven set at 150° C. for at least about 2 minutes in order to shrink the shrink tubing.

The pre-inflation balloon possessed 2.03 mm and 2.06 mm minimum and maximum dimensions, respectively, the balloon catheter was tested under pressure as described in Example 1. The inflated balloon possessed 5.29 mm and 5.36 mm minimum and maximum dimensions, respectively. The deflated balloon possessed 2.19 mm and 3.21 mm minimum and maximum dimensions, respectively. The resulting compaction efficiency and the compaction ratio were 0.68 and 0.64, respectively.

The pitch angles of the film were also measured pre-inflation, at inflation (8 atm), and at deflation, yielding values of about 20°, 50°, and 25°, respectively. The balloon was reinflated with 10 atm and the pitch angles of the film were measured for the inflation and deflation conditions. The angles were the same for both inflation pressures.

The balloon was subjected to even higher pressures to determine the pressure at failure. The balloon withstood 19.5 atm pressure prior to failure due to breakage of the shrink tubing at the distal end of the balloon. Another balloon catheter was made using a piece of the same balloon material, following the same procedures described in this example. This balloon catheter was used to distend a 3 mm GORE-TEX Vascular Graft (item no. V03050L, W. L. Gore and Associates, Inc., Flagstaff Ariz.) from which the outer reinforcing film had been removed. The graft was placed over the balloon such that the distal end of the graft was positioned approximately 1 cm from the distal end of the balloon. The balloon was inflated to 8 atm, the graft distended uniformly without moving in the longitudinal direction with respect to the balloon. Another piece of the same graft was tested in the same manner using a 6 mm diameter, 4 cm long Schneider Match 35 PTA Catheter (model no. B506-412). In this case, the graft slid along the length of the balloon proximally during the balloon inflation; the distal end of the graft was not distended.

Example 6

A balloon catheter was made following all of the steps of Example 5 with one exception in order to provide a balloon that bends during inflation.

All of the same steps were followed as in Example 5 with the exception of eliminating the manual elongation step that immediately followed the longitudinal compression step. That is, at the point of being impregnated with silicone dispersion, the film-covered porous PTFE tube was 0.6 of its initial length (instead of 0.8 as in Example 5).

A balloon catheter was constructed using this balloon. The length of the balloon was 4.0 cm. The bend of the balloon was tested by inflating the balloon to 8 atm and measuring the bend angle created by inflation. Measurements were made via the balloon aligned coincident with the 0° scribe line of a protractor, with the middle of the balloon positioned at the origin. The bend angle was 50°. The balloon was then bent an additional 90° and allowed to relax. No kinking occurred even at 140°. The angle of the still inflated, relaxed balloon stabilized at 90°.

The balloon of an intact 6 mm diameter, 4 cm long Schneider Match 35 PTA Catheter (model no. B506-412) was tested in the same manner. The bend angle under 8 atm pressure was 0°. The inflated balloon was then bent to 90°, which created a kink. The inflated balloon was allowed to relax. The balloon bend angle stabilized at 25°. The bending characteristics of an article of the present invention should enable the dilatation of a vessel and a side branch of the same vessel simultaneously. The inventive balloon is easily bendable without kinking. Kinking is defined as wrinkling of the balloon material.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A balloon having a longitudinal axis, said balloon comprising an elastomeric material, a first polytetrafluoroethylene material oriented substantially parallel to the longitudinal axis and a second polytetrafluoroethylene material oriented substantially circumferential to the longitudinal axis.

2. A balloon according to claim 1 wherein the elastomeric material is chosen from the group consisting of fluoroelastomers, silicones, latexes and polyurethanes.

3. A balloon according to claim 1 wherein the balloon has a substantially round transverse cross section when inflated and when subsequently deflated.

4. A balloon according to claim I used to distend a medical device.

5. A balloon according to claim 1 wherein said balloon following inflation to 5 atmospheres and subsequent deflation has a compaction ratio of greater than about 0.5.

6. A balloon according to claim 1 wherein said balloon during inflation exhibits a larger diameter at a first portion of its length than at a second portion.

7. A balloon according to claim 1 wherein an end of said balloon is elastomer-impregnated polytetrafluoroethylene material affixed to a catheter shaft.

8. A balloon according to claim 1 wherein said first and second polytetrafluoroethylene materials are porous polytetrafluoroethylene materials and wherein at least a portion of said elastomeric material is impregnated into the porous polytetrafluoroethylene materials.

9. A balloon having ,a longitudinal axis, said balloon comprising a first porous polytetrafluoroethylene material oriented substantially parallel to the longitudinal axis and a second porous polytetrafluoroethylene material oriented substantially circumferential to the longitudinal axis, wherein said balloon is capable of delivering a fluid through the first and second polytetrafluoroethylene materials.

10. A balloon cover for a balloon having a longitudinal axis, said balloon cover comprising an elastomeric material, a first polytetrafluoroethylene material oriented substantially parallel to the longitudinal axis and a second polytetrafluoroethylene material oriented substantially circumferential to the longitudinal axis.

11. A balloon cover according to claim 10 wherein the elastomeric material is chosen from the group consisting of fluoroelastomers, silicones, latexes and polyurethanes.

12. A balloon cover according to claim 10 wherein said first and second polytetrafluoroethylene materials are porous polytetrafluoroethylene materials and wherein at least a portion of said elastomeric material is impregnated into the porous polytetrafluoroethylene materials.

13. A method of making a balloon comprising:
   a) forming a tube from at least two layers of porous polytetrafluoroethylene; and b) impregnating the tube with an elastomer.

14. A method according to claim 13 wherein the balloon is affixed to a catheter shaft.

15. A method according to claim 13 wherein the method of forming the tube from at least two layers of porous polytetrafluoroethylene comprises:
   a) fitting a porous polytetrafluoroethylene tube over a mandrel;
   b) fitting at least one tube of helically wrapped porous polytetrafluoroethylene film over the porous polytetrafluoroethylene tube;
   c) applying tension to the tube of helically wrapped porous polytetrafluoroethylene film to cause it to fit snugly to the porous polytetrafluoroethylene tube;
   d) applying heat to the mandrel, the tube of helically wrapped porous polytetrafluoroethylene film and the porous polytetrafluoroethylene tube to create a reinforced tube; and
   e) removing the reinforced tube from the mandrel.

16. A method according to claim 15 wherein the balloon is affixed to a catheter shaft.

17. A method according to claim 15 wherein prior to impregnating the reinforced tube with an elastomer, longitudinal compression is applied to the reinforced tube thereby causing a reduction in length of the reinforced tube.

18. A method of using a balloon catheter having a balloon having a longitudinal axis, said balloon comprising an elastomeric material, a first polytetrafluoroethylene material oriented substantially parallel to the longitudinal axis and a second polytetrafluoroethylene material oriented substantially circumferential to the longitudinal axis, said method comprising a surgical vascular procedure selected from the group consisting of graft delivery, graft distension, stent delivery, stent distension and angioplasty.

* * * * *